US009315526B2

(12) United States Patent
Hagadorn et al.

(10) Patent No.: US 9,315,526 B2
(45) Date of Patent: Apr. 19, 2016

(54) PYRIDYLDIAMIDO TRANSITION METAL COMPLEXES, PRODUCTION AND USE THEREOF

(71) Applicant: ExxonMobil Chemical Patents Inc., Baytown, TX (US)

(72) Inventors: John R. Hagadorn, Houston, TX (US); Patrick J. Palafox, Pasadena, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/628,401

(22) Filed: Feb. 23, 2015

(65) Prior Publication Data
US 2015/0246982 A1  Sep. 3, 2015

Related U.S. Application Data

(60) Provisional application No. 61/947,052, filed on Mar. 3, 2014.

(51) Int. Cl.
C08F 4/76 (2006.01)
C08F 4/64 (2006.01)
C07F 7/00 (2006.01)
C08F 4/659 (2006.01)

(52) U.S. Cl.
CPC . C07F 7/00 (2013.01); C08F 4/659 (2013.01); C08F 4/65908 (2013.01); C08F 4/65912 (2013.01); C08F 4/65916 (2013.01)

(58) Field of Classification Search
CPC .............................. C08F 4/60148; C08F 4/76
See application file for complete search history.

(56) References Cited

U.S. PATENT DOCUMENTS

| | | | |
|---|---|---|---|
| 5,318,935 A | 6/1994 | Canich et al. | |
| 6,103,657 A | 8/2000 | Murray | |
| 6,175,409 B1 | 1/2001 | Nielsen et al. | |
| 6,194,527 B1 | 2/2001 | Cribbs | |
| 6,260,407 B1 | 7/2001 | Petro et al. | |
| 6,294,388 B1 | 9/2001 | Petro | |
| 6,306,658 B1 | 10/2001 | Turner et al. | |
| 6,406,632 B1 | 6/2002 | Safir et al. | |
| 6,436,292 B1 | 8/2002 | Petro | |
| 6,454,947 B1 | 9/2002 | Safir et al. | |
| 6,455,316 B1 | 9/2002 | Turner et al. | |
| 6,461,515 B1 | 10/2002 | Safir et al. | |
| 6,475,391 B2 | 11/2002 | Safir et al. | |
| 6,489,168 B1 | 12/2002 | Wang et al. | |
| 6,491,816 B2 | 12/2002 | Petro | |
| 6,491,823 B1 | 12/2002 | Safir et al. | |
| 6,521,793 B1 | 2/2003 | Guram et al. | |
| 6,610,805 B1 | 8/2003 | Guram et al. | |
| 6,683,141 B1 | 1/2004 | Gibson et al. | |
| 6,750,345 B2 | 6/2004 | Boussie et al. | |
| 6,900,321 B2 | 5/2005 | Boussie et al. | |
| 7,018,949 B2 | 3/2006 | Boussie et al. | |
| 7,041,765 B2 | 5/2006 | Tau et al. | |
| 7,045,583 B2 | 5/2006 | Kuchta et al. | |
| 7,102,006 B2 | 9/2006 | Vogel et al. | |
| 7,164,020 B2 | 1/2007 | Vogel | |
| 7,276,567 B2 | 10/2007 | Voskoboynikov et al. | |
| 7,425,661 B2 | 9/2008 | McConville et al. | |
| 7,446,216 B2 | 11/2008 | Voskoboynikov et al. | |
| 7,538,168 B2 | 5/2009 | Voskoboynikov et al. | |
| 7,557,171 B2 | 7/2009 | Voskoboynikov et al. | |
| 7,667,064 B2 | 2/2010 | Voskoboynikov et al. | |
| 7,812,104 B2 | 10/2010 | Canich et al. | |
| 7,868,197 B2 | 1/2011 | Voskoboynikov et al. | |
| 7,973,116 B2 | 7/2011 | Hagadorn et al. | |
| 2002/0142912 A1 | 10/2002 | Boussie et al. | |
| 2002/0156279 A1 | 10/2002 | Boussie et al. | |
| 2004/0220050 A1 | 11/2004 | Frazier et al. | |
| 2006/0135722 A1 | 6/2006 | Boussie et al. | |
| 2007/0191607 A1 | 8/2007 | Solan et al. | |
| 2010/0022726 A1* | 1/2010 | Hagadorn et al. | 526/154 |
| 2010/0227990 A1 | 9/2010 | Kuhlman et al. | |
| 2011/0224391 A1 | 9/2011 | Hagadorn et al. | |
| 2011/0301310 A1 | 12/2011 | Hagadorn et al. | |
| 2012/0071616 A1 | 3/2012 | Hagadorn et al. | |

FOREIGN PATENT DOCUMENTS

| | | |
|---|---|---|
| JP | 2001/048925 | 2/2001 |
| WO | 00/09255 | 2/2000 |
| WO | 02/38628 | 5/2002 |
| WO | 2005/095469 | 10/2005 |
| WO | 2007/067965 | 6/2007 |
| WO | 2010/037059 | 4/2010 |
| WO | 2012/134613 | 10/2012 |
| WO | 2012/134614 | 10/2012 |
| WO | 2012/134615 | 10/2012 |

OTHER PUBLICATIONS

U.S. Appl. No. 61/815,065, filed Apr. 23, 2013, Hagadorn et al.
Britovsek, George J.P. et al., "The Search for New-Generation Olefin Polymerization Catalysts: Life beyond Metallocenes," Angew. Chem. Int. Ed., 1999, vol. 38(4), pp. 428-447.
Boussie, Thomas R. et al., "A Fully Integrated High-Throughput Screening Methodology for the Discovery of New Polyolefin Catalysts: Discovery of a New Class of High Temperature Single-Site Group (IV) Copolymerization Catalysts," Journal Am. Chem. Soc., 2003, vol. 125, pp. 4306-4317.
Froese, R.D.J. et al, "Mechanism of Activation of a Hafnium Pyridyl-Amide Olefin Polymerization Catalyst: Ligand Modification by Monomer," Journal American Chemical Society, 2007, vol. 129, pp. 7831-7840.
Gibson, V.C. et al, S.K. Chem. Rev. 2003, vol. 103, p. 283.
Guérin, F. et al., "Synthesis, Structure, and Reactivity of Zirconium Alkyl Complexes Bearing Ancillary Pyridine Diamide Ligands," Organometallics, 1998, vol. 17, No. 23, pp. 5172-5177.
Guérin, F. et al., "Conformationally Rigid Diamide Complexes of Zirconium: Electron Deficient Analogues of Cp2Zr," Organometallics, 1996, vol. 15, pp. 5586.
Hagadorn, John R. et al., Early Metal Complexes Supported by Nitrogen-Donor Ligands and Their Use as Catalysts for the Polymerization of Olefins, American Chemical Society, 2011, vol. 51(1).
Vaughan, A. et al., "Industrial catalysts for alkene polymerization," Comprehensive Polymer Science, vol. 3, Chapter 20, 2012, pp. 657-671.

* cited by examiner

Primary Examiner — Rip A Lee

(57) ABSTRACT

Pyridyldiamido transition metal complexes are disclosed for use in alkene polymerization to produce high melting point polyolefins.

42 Claims, 1 Drawing Sheet

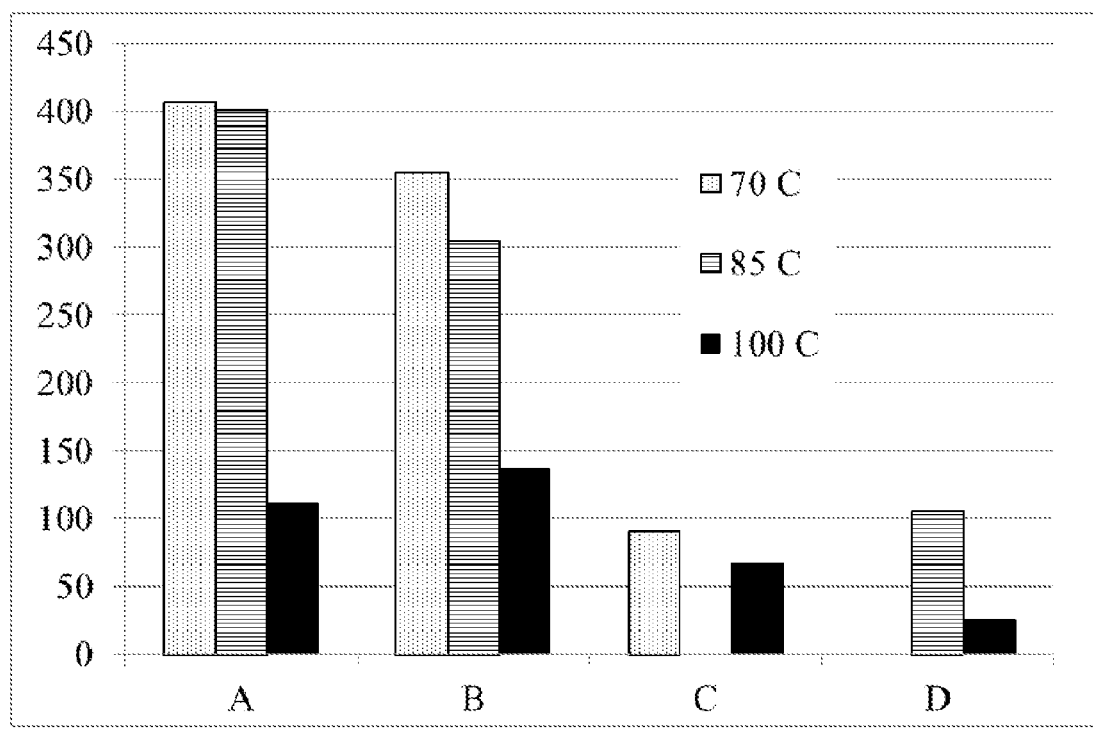

PYRIDYLDIAMIDO TRANSITION METAL COMPLEXES, PRODUCTION AND USE THEREOF

PRIORITY

This invention claims priority to and the benefit of U.S. Ser No., filed 61/947,052, filed Mar, 3, 2014.

FIELD OF INVENTION

The invention relates to pyridyldiamido transition metal complexes and intermediates and processes for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components in the polymerization of alkenes, see for example US 2002/0142912, U.S. Pat. Nos. 6,900,321, and 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, 7831-7840) to form an active catalyst that has both a five-membered and a seven-membered chelate ring.

WO 2010/037059 discloses pyridine containing amines for use in pharmaceutical applications.

US 2012/0071616 A1 discloses pyridyldiamide catalyst complexes incorporating an NNN ligand having a neutral pyridine donor and two anionic amide donors that are substituted with a phenyl group and a 2,6-diisopropylphenyl group, but not hydrocarbyl groups having 1 to 20 carbon atoms and having an H/C ratio of 1.66 or higher where the carbon atom bonded to the nitrogen is not a tertiary carbon atom.

Additional references of interest include: Vaughan, A; Davis, D. S.; Hagadorn, J. R. in Comprehensive Polymer Science, Vol. 3, Chapter 20, "Industrial catalysts for alkene polymerization;" Gibson, V. C.; Spitzmesser, S. K. Chem. Rev. 2003, 103, 283; Britovsek, G. J. P.; Gibson, V. C.; Wass, D. F. Angew. Chem. Int. Ed. 1999, 38, 428; U.S. Pat. Nos. 7,973,116; 7,446,216; 7,812,104; 7,276,567; 7,667,064; 7,868,197; 7,557,171; 7,538,168; US 2011/0224391; US 2011/0301310; U.S. Ser. No. 61/815065 filed Apr. 23, 2013; US 2010/0227990 (note catalyst structures bind to the metal center with a NNC donor set); WO/0238628 A2 (note ligands bind to the metal center with a NNC donor set); and Guerin, F.; McConville, D. H.; Vittal, J. J. *Organometallics* 1996, 15, 5586 (note NNN-donor set does not contain a 7-membered chelate ring or dihydroindenyl- and/or tetrahydronaphthalenyl-groups).

There still is need for adding synthetic routes to widen the range of catalysts complexes that may be prepared and broaden their performance in alkene polymerization. The performance may be varied with respect to the amount of polymer produced per amount of catalyst (generally referred to as the "activity") under the prevailing polymerization conditions; the molecular weight and molecular weight distribution achieved at a given temperature; and the placement of higher alpha-olefins in terms of the degree of stereoregular placement.

Further, improved catalyst productivity is desired because it reduces in use catalyst cost. Additionally, single-site catalysts that produce high molecular weight, highly crystalline polypropylene are rare, yet desired for the production of polypropylene containing products of high stiffness.

This need is addressed by the new pyridyldiamide (PDA) catalysts disclosed herein. In propylene polymerization studies, these catalysts were found to have both improved activity and to produce higher melting point polymer.

SUMMARY OF INVENTION

This invention relates to novel transition metal complexes having tridentate NNN or PNN ligands. This invention also relates to pyridyldiamido and related transition metal complexes represented by the formula (A), (B), (I), or (II):

(A)

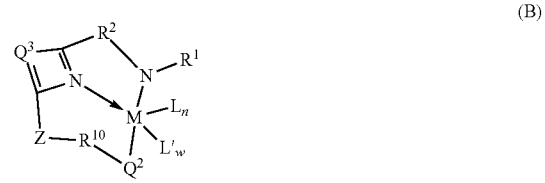

(B)

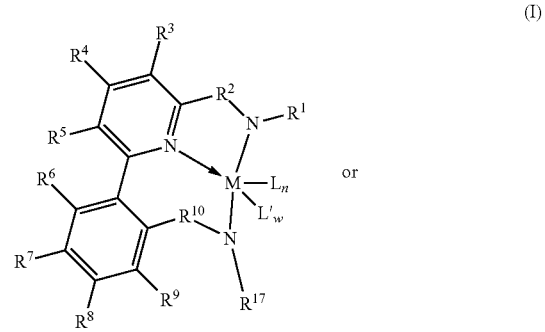

(I)

or

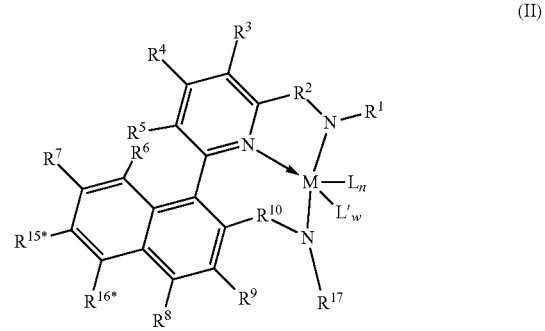

(II)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that preferably forms a dative bond to M preferably represented by the formula: -$G^1$-$G^2$-$G^3$- where $G^2$ is a group 15 or 16 atom, $G^1$ and $G^3$ are each a group 14, 15 or 16 atom, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$ and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is $NR^{17}$ or $PR^{17}$, where $R^{17}$ is selected from hydrocarbyl groups containing 1 to 20 carbon atoms having a H/C ratio of 1.66 or more where the carbon atom bonded to the N or P is not a tertiary carbon atom, and where $R^{17}$ may be unsubstituted or substituted;

$Q^3$ is -(TT)- or -(TTT)- where each T is carbon or a heteroatom (preferably C, O, S, or N, and said carbon or heteroatom may be unsubstituted (e.g., hydrogen is bound to the carbon or heteroatom) or substituted with one or more $R^{30}$ groups), that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —($R_{14}$)$_p$C—C($R_{15}$)$_q$— and $R_{14}$ and $R_{15}$ are independently selected from the group consisting of hydrogen, hydrocarbyls, and substituted hydrocarbyls, and wherein adjacent $R_{14}$ and $R_{14}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n+w is no greater than 4;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings; and $R^6$, $R^7$, $R^8$, $R^9$, $R^{15}*$, and $R^{16}*$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}*$, and/or $R^{16}*$ & $R^{15}*$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings.

This invention also relates to a process to make polyolefin, such as polypropylene, using the catalysts described herein, where the catalyst has an activity of 200 kg polymer/mmol catalyst/h or more.

This invention further relates to process to make the above complex, process to make intermediates for the above complex and methods to polymerize olefins using the above complex, where the complex has an activity of 200 kg polymer/mmol catalyst/h or more.

BRIEF DESCRIPTION OF THE DRAWINGS

FIG. 1 is a plot showing the catalyst activity in kg polymer/mmol catalyst/h for catalysts formed by activation of complexes A, B, C and D.

DETAILED DESCRIPTION

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

Unless otherwise indicated, room temperature is 23° C.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and $^t$Bu are tertiary butyl, Pr is propyl, iPr and $^i$Pr are isopropyl, Cy is cyclohexyl, THF (also referred to as thf) is tetrahydrofuran, Bn is benzyl, OAc is acetate and Ph is phenyl.

The term "substituted" generally means that a hydrogen of the substituted species has been replaced with a different atom or group of atoms. For example, methyl-cyclopentadiene is cyclopentadiene that has been substituted with a methyl group. Likewise, picric acid can be described as phenol that has been substituted with three nitro groups, or, alternatively, as benzene that has been substituted with one hydroxy and three nitro groups.

The terms "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

A substituted hydrocarbyl radical is a hydrocarbyl radical in which at least one hydrogen atom of the hydrocarbyl radical has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is typically a polymer having a low molecular weight (such an Mn of less than 25,000 g/mol, preferably less than 2,500 g/mol) or a low number of mer units (such as 75 mer units or less). An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

A higher α-olefin or higher alkyl is defined to be an α-olefin having 4 or more carbon atoms.

Unless otherwise noted, all molecular weights units (e.g., Mw, Mn, Mz) are g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or thee ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

The term "aromatic" refers to benzene and derivatives of benzene, which are cyclic hydrocarbyl groups having six carbons in a ring with three alternating double bonds. As used herein the term "aromatic" also refers to cyclopentadienes and pseudoaromatic heterocycles which are heterocyclic substituents that have similar properties and structures (nearly planar) to aromatic heterocyclic ligands, but are not by definition aromatic; likewise, the term aromatic also refers to substituted aromatics.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

The term "multimodal," when used to describe a polymer or polymer composition, means "multimodal molecular weight distribution," which is understood to mean that the Gel Permeation Chromatography (GPC) trace, plotted as Absorbance versus Retention Time (seconds), has more than one peak or inflection points. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition. Preferably the Mw's of the polymer or polymer composition differ by at least 10%, relative to each other, preferably by at least 20%, preferably at least 50%, preferably by at least 100%, preferably by a least 200%. Likewise, in a preferred embodiment, the Mw's of the polymer or polymer composition differ by 10% to 10,000%, relative to each other, preferably by 20% to 1000%, preferably 50% to 500%, preferably by at least 100% to 400%, preferably 200% to 300%.

Unless otherwise indicated "catalyst activity" is a measure of how many kilograms of polymer (P) are produced using a polymerization catalyst comprising W mmol of transition metal (M), over a period of time of T hours; and may be expressed by the following formula: P/(T×W).

In a first aspect of the invention there is provided a pyridyldiamido transition metal complex (optionally for use in alkene polymerization) represented by the formula (A) or (B):

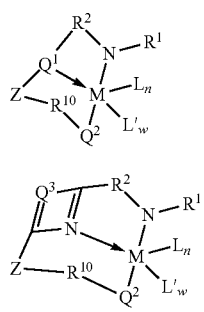

wherein:

M is a Group 3, 4, 5, 6, 7, 8, 9, 10, 11, or 12 metal, preferably group 4;

$Q^1$ is a group that links $R^2$ and Z by a three atom bridge with the central of the three atoms being a group 15 or 16 element that preferably forms a dative bond to M, preferably represented by the formula: -$G^1$-$G^2$-$G^3$- where $G^2$ is a group 15 or 16 atom (preferably N, S, P, or O, preferably N or P, preferably N), $G^1$ and $G^3$ are each a group 14, 15, or 16 atom, preferably C, Si, N, S, P, or 0 (preferably C), where $G^1$, $G^2$ and $G^3$, or $G^1$ and $G^2$, or $G^1$ and $G^3$, or $G^2$ and $G^3$ may form a singular or multi ring system, and if either of $G^1$ and/or $G^3$ is a group 14 atom (such as C or Si) then $R^{30}$ and $R^{31}$ are bound to such G atom(s), and if $G^1$, $G^2$, and/or $G^3$ is a group 15 atom (such as N or P) then $R^{30}$ is bound to such G atom(s), where each $R^{30}$ and $R^{31}$ is, independently, hydrogen or a $C_1$ to $C_{100}$ hydrocarbyl group (alternately a $C_1$ to $C_{40}$, alternately a $C_1$ to $C_{20}$ hydrocarbyl group);

$Q^2$ is $NR^{17}$ or $PR^{17}$, where $R^{17}$ is selected from hydrocarbyl groups containing 1 to 20 carbon atoms (preferably from 2 to 16, preferably from 4 to 14, preferably from 5 to 12, preferably from 6 to 10) having a H/C ratio of 1.66 or more (alternately 1.70 or more, alternately 1.80 or more, alternately 1.83 or more) where the carbon atom bonded to the N or P is not a tertiary carbon atom, and where $R^{17}$ may be unsubstituted or substituted with between one to five substituents that include F, Cl, Br, I, $CF_3$, $NO_2$, alkoxy, dialkylamino, silyl, siloxy, aryloxy, aryl, and alkyl groups having 1 to 10 carbons, such as methyl, ethyl, propyl, butyl, pentyl, hexyl, heptyl, octyl, nonyl, decyl, and isomers thereof;

$Q^3$ is -(TT)- or -(TTT)- where each T is carbon or a heteroatom, preferably C, O, S, or N, and said carbon or heteroatom may be unsubstituted (e.g., hydrogen is bound to the carbon or heteroatom) or substituted with one or more $R^{30}$ groups), that together with the "—C-$Q^3$=C—" fragment, forms a 5- or 6-membered cyclic group or a polycyclic group including the 5- or 6-membered cyclic group;

$R^1$ is selected from the group consisting of hydrocarbyls, and substituted hydrocarbyls, or silyl groups;

$R^2$ and $R^{10}$ are each, independently, -$E(R^{12})(R^{13})$— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —$(R_{14})_pC$—$C(R_{15})_q$—, where $R^{14}$ and $R^{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3, or 4;

wherein n+w is no greater than 4.

The H/C ratio is the ratio of number of hydrogen atoms to number of carbon atoms. For example, a methyl group ($C_1$-$H_3$) has an H/C ratio of 3, while a cyclohexyl ($C_6$-$C_{11}$) group has an H/C ratio of 1.83, a phenyl group ($C_6H_5$) has an H/C ratio of 0.83, and a tetradecylphenyl group ($C_{20}H_{33}$) has an H/C ratio of 1.65.

In another aspect of the invention there is provided a pyridyldiamido transition metal complex (optionally for use in alkene polymerization) represented by the formula (I) or (II):

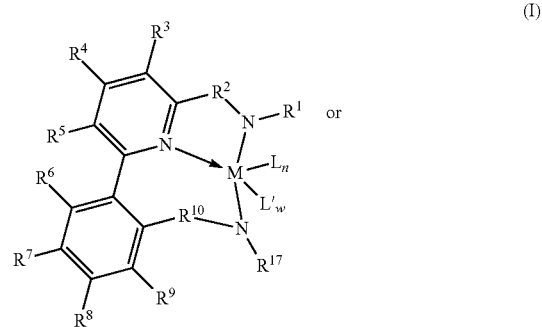

-continued

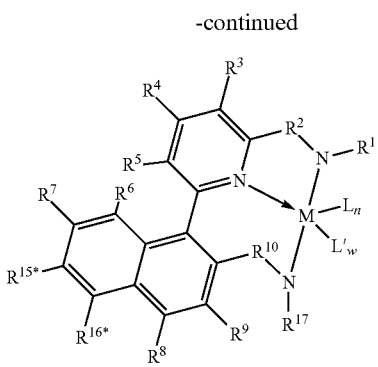

(II)

wherein:
M is a Group 3, 4, 5, 6, 7, 8, 9, 10, 11, or 12 metal, preferably group 4; each $R^1$ is independently selected from the group consisting of hydrocarbyls, and substituted hydrocarbyls, or silyl groups;
$R^2$ and $R^{10}$ are each, independently, $-E(R^{12})(R^{13})-$ with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;
$R^{17}$ is selected from hydrocarbyl groups containing 1 to 20 carbon atoms (preferably from 2 to 16, preferably from 4 to 14, preferably from 5 to 12, preferably from 6 to 10) having a H/C ratio of 1.66 or more (alternately 1.70 or more, alternately 1.80 or more, alternately 1.83 or more) where the carbon atom bonded to the N is not a tertiary carbon atom (preferably the carbon atom bonded to the N is a secondary or primary carbon atom), and where $R^{17}$ may be unsubstituted or substituted with between one to five substituents that include F, Cl, Br, I, $CF_3$, $NO_2$, alkoxy, dialkylamino, silyl, siloxy, aryloxy, aryl, and alkyl groups having 1 to 10 carbons, such as methyl, ethyl, propyl, butyl, pentyl, hexyl, heptyl, octyl, nonyl, decyl, and isomers thereof;
$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;
$R^6$, $R^7$, $R^8$, $R^9$, $R^{15*}$, and $R^{16*}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15*}$, and/or $R^{16*}$ & $R^{15*}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;
L is an anionic leaving group, where the L groups may be the same or different and any two L groups may be linked to form a dianionic leaving group;
n is 0, 1, 2, 3, or 4;
L' is neutral Lewis base; and
w is 0, 1, 2, 3, or 4;
wherein n+w is not greater than 4.

In a preferred embodiment of the invention, $Q^1$ is a substituted or unsubstituted pyridine group linked to Z and $R^2$ through the carbons in the 2 and 6 position (of the pyridine ring, with the nitrogen being the 1 position).

In a preferred embodiment of the invention, $G^1$ and $G^3$ are each independently selected from C, N, O, and S, preferably $G^1$ and $G^3$ with their respective R groups are methyl, ethyl, propyl, butyl, pentyl, hexyl, octyl, and the like, preferably $G^1$ and $G^3$ with their respective R groups are formed into a ring structure, preferably pyridine.

In an alternate embodiment of the invention, $R^{17}$ is selected from hydrocarbyl groups containing 1 to 20 carbon atoms (preferably from 2 to 16, preferably from 4 to 14, preferably from 5 to 12, preferably from 6 to 10) having a H/C ratio of 1.66 or more (alternately 1.70 or more, alternately 1.80 or more, alternately 1.83 or more) where the carbon atom bonded to the N (or P in $Q_2$ of formula A or B) is a primary or secondary carbon atom, preferably secondary carbon atom.

In any embodiment of the invention, $R^{17}$ is non-aromatic.

In any embodiment of the invention, $R^{17}$ may be selected from cyclic (preferably non-aromatic) hydrocarbyls, cyclic (preferably non-aromatic) substituted hydrocarbyls, and cyclic (preferably non-aromatic) silyl groups.

In any embodiment of the invention, $R^{17}$ is a saturated $C_5$ to $C_{12}$ cyclic group or a substituted non aromatic $C_5$ to $C_{12}$ cyclic group, preferably a cyclic, saturated alkyl group having 3 to 20 carbons, such as cyclopropyl, cyclobutyl, cyclopentyl, cyclohexyl, cycloheptyl, cyclooctyl, cyclononyl, cyclodecyl, cyclododecyl, or an isomer thereof.

In any embodiment of the invention, $R^{17}$ is selected from methyl, primary alkyls, branched primary alkyls, secondary alkyls, and cycloalkyls, such as methyl, ethyl, propyl, n-butyl, cyclohexyl, cyclooctyl, and cyclododecyl, provided that the carbon atom bonded to the N or P is a primary or secondary carbon atom, preferably secondary carbon atom.

In any embodiment of the invention, $R^{17}$ is an n-alkyl group or a cyclic aliphatic hydrocarbon group.

In a preferred embodiment of the invention, $Q^2$ is $NR^{17}$.

In a preferred embodiment of the invention, $Q^3$ is a three carbon linker (CH—CH—CH) that forms a pyridine ring. In another preferred embodiment, $Q^3$ is two atom linker containing one carbon and one group 15 or 16 element such that the linker forms a five-membered heterocycle, such as an imidazole or a substituted imidazole.

Preferably, the R groups above and other R groups mentioned hereafter, contain from 1 to 30, preferably 2 to 20 carbon atoms, especially from 6 to 20 carbon atoms.

Preferably, M is Ti, Zr, or Hf, and/or E is carbon, with Zr or Hf based complexes being especially preferred.

In a preferred embodiment of the invention, $R^1$ is selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In a preferred embodiment, L may be selected from halide, alkyl, aryl, alkoxy, amido, hydrido, phenoxy, hydroxy, silyl, allyl, alkenyl, and alkynyl. The selection of the leaving groups depends on the synthesis route adopted for arriving at the complex and may be changed by additional reactions to suit the later activation method in polymerization. For example, a preferred L is alkyl when using non-coordinating anions such as N,N-dimethylanilinium tetrakis(pentafluorophenyl)borate or tris(pentafluorophenyl)borane. In another embodiment, two L groups may be linked to form a dianionic leaving group, for example oxalate.

In another embodiment, each L' is independently selected from the group consisting of ethers, thio-ethers, amines, nitriles, imines, pyridines, and phosphines, preferably ethers.

Preferred $R^2$ groups and preferred $R^{10}$ groups include $CH_2$, $CMe_2$, $SiMe_2$, $SiEt_2$, $SiPr_2$, $SiBu_2$, $SiPh_2$, $Si(aryl)_2$, $Si(alkyl)_2$, CH(aryl), CH(Ph), CH(alkyl), and CH(2-isopropylphenyl).

Preferred pairing of $R^2$ and $R^{10}$ groups (expressed as $R^2$ & $R^{10}$) includes: ($CH_2$ & CH(Ph)), ($CMe_2$ and CH(Ph)), ($CH_2$ and CH(aryl)), ($CH_2$ and CH(alkyl)), where alkyl is a $C_1$ to $C_{40}$ alkyl group (preferably $C_1$ to $C_{20}$ alkyl, preferably one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (preferably a $C_6$ to $C_{20}$ aryl group, preferably phenyl or substituted phenyl, preferably phenyl, 2-isopropylphenyl, or 2-tertbutylphenyl).

In another embodiment, $R^2$ is $CH_2$ or $CMe_2$ and $R^{10}$ is selected from the group consisting of CH(Ph), CH(aryl), and CH(alkyl), where alkyl is a $C_1$ to $C_{40}$ alkyl group (preferably $C_1$ to $C_{20}$ alkyl, preferably one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (preferably a $C_6$ to $C_{20}$ aryl group, preferably phenyl or substituted phenyl, preferably phenyl, 2-isopropylphenyl, or 2-tertbutylphenyl).

In any embodiment described herein, E is preferably carbon.

In any embodiment described herein, $R^2$ is represented by the formula:

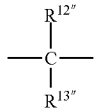

where $R^{12''}$ is hydrogen, alkyl, aryl, or halogen; and $R^{13''}$ is hydrogen, alkyl, aryl, or halogen, preferably $R^{12''}$ and $R^{13''}$ are the same.

In any embodiment described herein, $R^6$, $R^7$, $R^8$, $R^9$, $R^{15*}$, and $R^{16*}$ may be, independently, selected from the group consisting of hydrogen, hydrocarbyls, substituted hydrocarbyls, alkoxy, halogen, amino, and silyl.

In any embodiment described herein, $R^1$, $R^3$, $R^4$, and $R^5$ may each contain from 1 to 30 carbon atoms, preferably $R^1$, $R^3$, $R^4$, $R^5$, $R^6$, $R^7$, $R^8$, $R^9$, $R^{15}$, and $R^{16}$ each contain from 1 to than 30 carbon atoms.

In any embodiment described herein, E is carbon and $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

In a preferred embodiment, the pyridyldiamido transition metal complex is represented by the Formula (A) or (B) above, and M is a Group 4 metal preferably Zr or Hf, preferably Hf.

In a preferred embodiment, the pyridyldiamido transition metal complex is represented by the Formula (I) or (II) above, and M is a Group 4 metal preferably Zr or Hf, preferably Hf.

In a preferred embodiment, the pyridyldiamido transition metal complex is represented by the Formula (A), (B), (I) or (II) above, and in the $R^{10}$ group $R^{12}$ and $R^{13}$ are H and $R^1$ is a 2,6-disubstituted phenyl group containing between 12 to 20 (preferably 12 to 15) carbons, M is a Group 4 metal (preferably Zr or Hf, preferably Hf), E is carbon, in the $R^2$ group $R^{12}$ is H and $R^{13}$ is preferably a hydrocarbon group containing between 6 and 20 carbons, and $R^{17}$ is a group containing 1 to 20 carbons and having a H/C ratio that is 1.66 or higher.

In a preferred embodiment, the pyridyldiamido transition metal complex is represented by the Formula (A), (B), (I) or (II) above, and both $R^{12}$ and $R^{13}$ in the $R^2$ group are a $C_1$ to $C_{100}$ alkyl group (preferably a $C_6$ to $C_{40}$ alkyl group, preferably $C_6$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In a preferred embodiment, the pyridyldiamido transition metal complex is represented by the Formula (A), (B), (I) or (II) above, and in the $R^2$ group $R^{12}$ is H, $R^{13}$ is a group containing between 1 to 100 (preferably 6 to 40, preferably 6 to 30) carbons, M is a Group 4 metal (preferably Zr or Hf, preferably Hf), E is carbon, in the $R^{10}$ group $R^{12}$ is the same as $R^{13}$ and is preferably hydrogen or methyl; and $R^{17}$ is a group containing 1 to 20 carbons and having a H/C ratio that is 1.66 or higher.

In a second aspect of the invention there are provided various processes for synthesizing the complexes described herein.

Ligand Synthesis

The pyridyl diamine ligands described herein are generally prepared in multiple steps. One step involves the preparation of an amine-containing "linker" group where the linker is typically a boronic acid ester of an aryl methyl amine or substituted amine This amine-containing linker may be prepared from an aryl-methyl boronic ester in two steps, the first of which involves the conversion of the methyl group to a halo-methyl group by free radical halogenation in unreactive solvents (e.g., $CCl_4$, benzene). The second step then involves reaction of this halo-methyl group containing species with an amine or protected amine or deprotonated protected amine to yield an amine-containing linker. This amine-containing linker is then coupled with a suitable pyridine containing species, such as 6-bromo-2-pyridinecarboxaldehyde. This coupling step typically uses a metal catalyst (e.g., $Pd(PPh_3)_4$) in less than 5 mol % loading. Following this coupling step, the new derivative, which can be described as amine-linker-pyridine-aldehyde, is then reacted with a second amine to produce the imine derivative amine-linker-pyridine-imine in a condensation reaction. This can then be reduced to the pyridyl diamine ligand by reaction with a suitable aryl anion, alkyl anion, or hydride source. This reaction is generally performed in etherial solvents at temperatures between –100° C. and 50° C. when aryllithium or alkyllithium reagents are employed. This reaction is generally performed in methanol at reflux when sodium cyanoborohydride is employed. The pyridyldiamine product and intermediate amine-containing products can be purified either using column chromatography or by procedures involving the formation of acid salts, such as that described in example 2 in U.S. Pat. No. 8,212,047 B2.

The preparation of pyridyl diamide metal complexes from pyridyl diamines may be accomplished using typical protonolysis and methylation reactions. In the protonolysis reaction the pyridyl diamine is reacted with a suitable metal reactant to produce a pyridyldiamide metal complex. A suitable metal reactant will feature a basic leaving group that will accept a proton from the pyridiyl diamine and then generally depart and be removed from the product. Suitable metal reactants include, but are not limited to, $HfBn_4$ (Bn=$CH_2Ph$), $ZrBn_4$, $TiBn_4$, $ZrBn_2Cl_2(OEt_2)$, $HfBn_2Cl_2(OEt_2)_2$, $Zr(NMe_2)_2Cl_2$(dimethoxyethane), $Hf(NMe_2)_2Cl_2$ (dimethoxyethane), $Hf(NMe_2)_4$, and $Hf(NEt_2)_4$. Pyridyldiamide (PDA) metal complexes that contain metal-chloride groups, such as the PDA dichloride complex in Scheme 1 below, can be alkylated by reaction with an appropriate organometallic reagent. Suitable reagents include organolithium and organomagnesium, and Grignard reagents. The alkylations are generally performed in etherial or hydrocarbon solvents or solvent mixtures at temperatures typically ranging from −100° C. to 50° C.

hour. For propylene polymerizations performed at 70° C. the substitution at the $R_{17}$ group with a cyclohexyl group has yielded catalysts capable of forming polypropylene with an activity of over 300 kg/mmol/hr, whereas the catalyst with $R_{17}$ being phenyl demonstrated an activity of 91 kg/mmol/hr. For propylene polymerizations performed at 85° C. the sub-

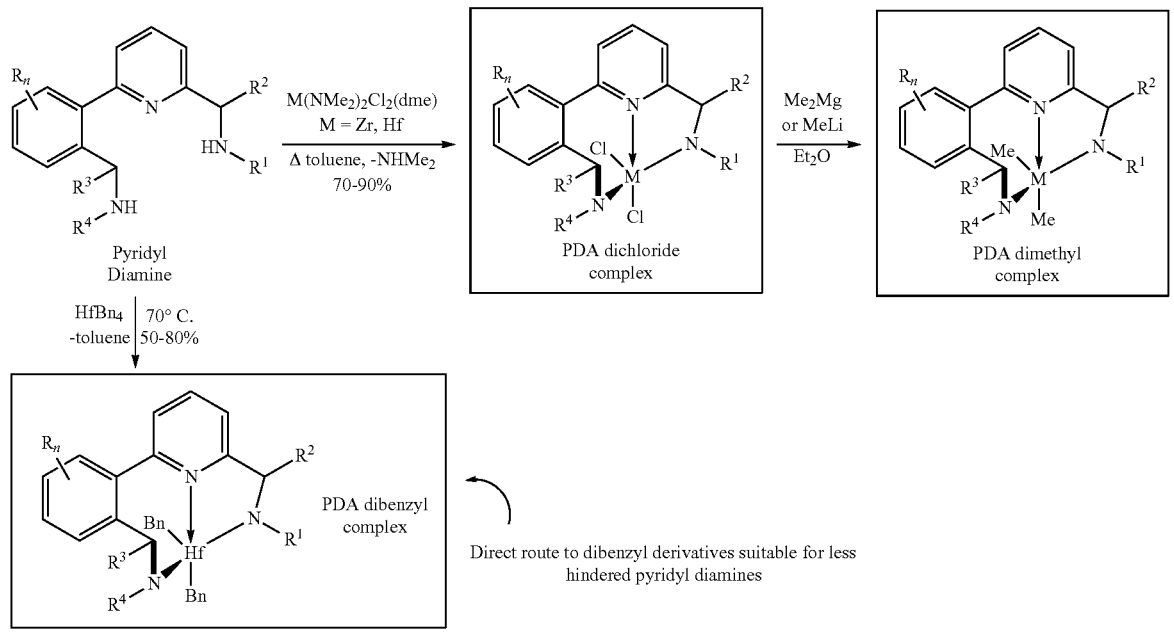

Scheme 1 where in Scheme 1, R, $R^1$, $R^2$, and $R^3$ are independently selected from the group consisting of H, hydrocarbyls (such as alkyls, aryls), substituted hydrocarbyls (such as heteroaryls), and silyl groups, and $R_n$, indicates hydrogen, hydrocarbyls, or substituted hydrocarbyls, which may be joined to form polycyclic aromatic rings and n is 1, 2, 3, or 4; and $R^4$ is selected from the group consisting of $C_1$ to $C_{20}$ non aromatic hydrocarbyl groups, preferably cyclic groups.

Another route to pyridyldiamide complexes is to deprotonate the pyridyldiamine with at least two equivalents of a base, such as butyllithium, to form a dilithium pyridyldiamide species. This lithium salt then may be reacted with a metal halide, such as $HfCl_4$ or $ZrCl_4$, to form a pyridyldiamide complex.

The choice of the $R^{17}$ group of the pyridyldiamide complexes can have a large effect on the polymerization activity of the activated complex and on the properties of the polymer produced. In particular, a cyclohexyl at the $R^{17}$ position (as opposed to a phenyl group) has been found to increase catalyst activity dramatically for propylene polymerization. Additionally, the melting point of the polypropylene produced is much higher for the cyclohexyl substituted catalysts. Without wishing to be bound by theory, the inventors suggest that the use of a non-aromatic hydrocarbon group in the $R^{17}$ position is advantageous because these groups increase the donor ability of the amido nitrogen to which they are bound. Other groups that are more electron donating than a phenyl group may also be desirable, such as methyl, ethyl, propyl, primary alkyls, branched primary alkyls, secondary alkyl, cycloalkyls, and tertiary alkyls.

Activity is described as kg of polymer produced per mmol of transition metal from the pyridyldiamide complex per stitution at the $R_{17}$ group with a cyclohexyl group has yielded catalysts capable of forming polypropylene with an activity of over 300 kg/mmol/hr, whereas the catalyst with $R_{17}$ being phenyl demonstrated an activity of 100 kg/mmol/hr. For propylene polymerizations performed at 100° C. the substitution at the $R_{17}$ group with a cyclohexyl group has yielded catalysts capable of forming polypropylene with an activity of over 110 kg/mmol/hr, whereas the catalysts with $R_{17}$ being phenyl demonstrated an activity of less than 70 kg/mmol/hr.

This invention also relates to a process to make polyolefin, such as polypropylene, using the catalysts described herein, where the catalyst has an activity of 200 kg polymer/mmol catalyst/h or more, preferably an activity of 200 kg pol/mmol catalyst/h or more for propylene polymerizations performed at 70° C. using conditions described in runs 1-3 in the examples.

This invention further relates to process to make the above complex, process to make intermediates for the above complex and methods to polymerize olefins using the above complex, where the complex has an activity of 200 kg polymer/mmol catalyst/h or more, preferably an activity of 200 kg pol/mmol catalyst/h or more for propylene polymerizations performed at 70° C. using conditions described in runs 1-3 in the examples.

Activators

After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer).

The catalyst system typically comprise a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis (pentafluorophenyl)borate (i.e., [PhNMe$_2$H]B(C$_6$F$_5$)$_4$) and N,N-dimethylanilinium tetrakis (heptafluoronaphthyl)borate, where Ph is phenyl, and Me is methyl.

Additionally, preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately, a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277 003 A1, and EP 0 277 004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (II):

$$(Z)_d^+(A^{d-}) \tag{II}$$

wherein Z is (L-H) or a reducible Lewis Acid, L is an neutral Lewis base; H is hydrogen; (L-H)$^+$ is a Bronsted acid; A$^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L-H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl. In a preferred embodiment, the reducible Lewis acid is triphenyl carbenium.

The anion component $A^{d-}$ include those having the formula $[M^{k+}Q_n]^{d-}$ wherein k is 1, 2, or 3; n is 1, 2, 3, 4, 5, or 6, preferably 3, 4, 5 or 6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene and or propylene) with the catalyst compound and a boron containing NCA activator represented by the formula (14):

$$Z_d^+(A^{d-}) \tag{14}$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d⁻ (as further described above); d is 1, 2, or 3.

In a preferred embodiment in any NCA's represented by Formula 14 described above, the reducible Lewis acid is represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's represented by Formula 14 described above, $Z_d^+$ is represented by the formula: $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

In a preferred embodiment in any of the NCA's represented by Formula 14 described above, the anion component $A^{d-}$ is represented by the formula $[M^{*k*+}Q^*_{n*}]^{d*-}$ wherein k* is 1, 2, or 3; n* is 1, 2, 3, 4, 5, or 6 (preferably 1, 2, 3, or 4); n*–k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and or propylene) with the catalyst compound and an NCA activator represented by the formula (I):

$$R_n M^{**}(ArNHal)_{4-n} \tag{I}$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula I also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula I described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; —$SR^1$, —$NR_2^2$, and —$FR_2^3$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula I described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula I described above, the NCA also comprises a cation represented by the formula, $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the formula (16):

$$(OX^{e+})_d(A^{d-})_e \tag{16}$$

wherein $OX^{e+}$ is a cationic oxidizing agent having a charge of e+; e is 1, 2, or 3; d is 1, 2 or 3; and $A^{d-}$ is a non-coordinating anion having the charge of d− (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis(pentafluorophenyl)borate.

In another embodiment, the catalyst compounds can be used with Bulky activators. A "Bulky activator" as used herein refers to anionic activators represented by the formula:

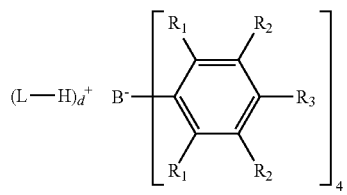

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably
$R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is an neutral Lewis base; $(L-H)^+$ is a Bronsted acid; d is 1, 2, or 3;
wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_S$, where $V_s$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_S$ | MV Per subst. (Å³) | Total MV (Å³) |
| --- | --- | --- | --- | --- | --- |
| Dimethylanilinium tetrakis(perfluoronaphthyl)borate | | $C_{10}F_7$ | 34 | 261 | 1044 |
| Dimethylanilinium tetrakis(perfluorobiphenyl)borate | | $C_{12}F_9$ | 42 | 349 | 1396 |

| Activator | Structure of boron substituents | Molecular Formula of each substituent | MV Per subst. $V_S$ (Å$^3$) | Total MV (Å$^3$) |
|---|---|---|---|---|
| [4-tButyl-PhNMe$_2$H] [(C$_6$F$_3$(C$_6$F$_5$)$_2$)$_4$B] | 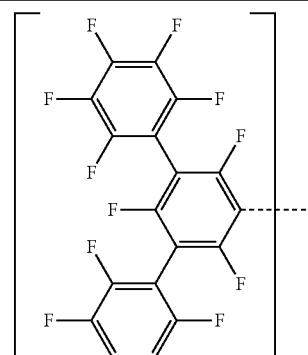 | C$_{18}$F$_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe$_2$H][(C$_6$F$_3$(C$_6$F$_5$)$_2$)$_4$B], and the types disclosed in U.S. Pat. No. 7,297,653.

Illustrative, but not limiting, examples of boron compounds which may be used as an activator in the processes of this invention are: N,N-dimethylanilinium tetrakis(perfluorophenyl)borate; methyldioctadecylammonium tetrakis(perfluorophenyl)borate; methyldi(C$_{14}$-$_{20}$ alkyl)ammonium tetrakis(perfluorophenyl)borate; trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis (perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts, such as: di-(i-propyl)ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^{-}]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium)tetrakis(pentafluorophenyl)borate, trialkylammonium tetrakis-(2,3,4,6-tetrafluorophenyl)borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

Supports

In some embodiments, the complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 μm. Some embodiments select a surface area of 50-500 $m^2/g$, a pore volume of 0.5-3.5 cc/g, or an average particle size of 20-200 μm. Other embodiments select a surface area of 100-400 $m^2/g$, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Inventive catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen, or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and optionally also polyenes (such as dienes).

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1,4-methylpentene-1,3-methylpentene-1,3,5,5-trimethylhexene-1, and 5-ethylnonene-1.

In a particularly preferred embodiment, propylene polymer, such as propylene homopolymer is produced.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157 and 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In a preferred embodiment, two or more complexes are combined with diethyl zinc in the same reactor with monomer. Alternately, one or more complexes is combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

In some embodiments herein, a multimodal polyolefin composition is produced, comprising a first polyolefin component and at least another polyolefin component, different from the first polyolefin component by molecular weight, preferably such that the GPC trace has more than one peak or inflection point.

In a preferred embodiment of the invention, a propylene polymer (such as homopolypropylene) is produced having a melting point (Tm, DSC, second melt) of 150° C. or more, preferably 151° C. or more, preferably 152° C. or more, preferably 153° C. or more, preferably 154° C. or more, preferably 155° C. or more, preferably 156° C. or more. For purposes of the claims, the Tm shall be determined as follows:

Differential Scanning Calorimetry (DSC)

Tm, Melting temperature (also referred to as melting point), is measured using Differential Scanning Calorimetry (DSC) on a commercially available instrument (e.g., TA Instruments 2920 DSC). Typically, 6 to 10 mg of molded polymer are sealed in an aluminum pan and loaded into the instrument at room temperature. Melting data (first heat) is acquired by heating the sample to at least 30° C. above its melting temperature, typically 220° C. for polypropylene, at a heating rate of 10° C./min. The sample is held for at least 5 minutes at this temperature to destroy its thermal history. Crystallization data are acquired by cooling the sample from the melt to at least 50° C. below the crystallization temperature, typically −50° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed according to standard procedures. The melting temperatures reported are the peak melting temperatures from the second heat unless otherwise specified. For polymers displaying multiple peaks, the melting temperature is defined to be the peak melting temperature from the melting trace associated with the largest endothermic calorimetric response (as opposed to the peak occurring at the highest temperature).

Measurements of weight average molecular weight (Mw), number average molecular weight (Mn), and z average molecular weight (Mz) are determined by Gel Permeation Chromatography (GPC) as described in Macromolecules, 2001, Vol. 34, No. 19, pg. 6812, which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument is operated with a flow rate of 1.0 cm³/min, and an injection volume of 300 μL. The various transfer lines, columns and differential refractometer (the DRI detector) are housed in an oven maintained at 145° C. Polymer solutions are prepared by heating 0.75 to 1.5 mg/mL of polymer in filtered 1,2,4-Trichlorobenzene (TCB) containing ~1000 ppm of butylated hydroxy toluene (BHT) at 160° C. for 2 hours with continuous agitation. A sample of the polymer containing solution is injected into to the GPC and eluted using filtered 1,2,4-trichlorobenzene (TCB) containing ~1000 ppm of BHT. The separation efficiency of the column set is calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000,000, were used to generate the calibration curve. The flow rate is calibrated for each run to give a common peak position for a flow rate marker (taken to be the positive inject peak) before determining the retention volume for each polystyrene standard. The flow marker peak position is used to correct the flow rate when analyzing samples. A calibration curve (log (Mp) vs. retention volume) is generated by recording the retention volume at the peak in the DRI signal for each PS standard, and fitting this data set to a 2nd-order polynomial. The equivalent polyethylene molecular weights are determined by using the Mark-Houwink coefficients shown in Table B.

TABLE B

| Mark-Houwink coefficients | | |
|---|---|---|
| Material | K (dL/g) | α |
| PS | 1.75 × 10⁻⁴ | 0.67 |
| PE | 5.79 × 10⁻⁴ | 0.695 |

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC and have a Tm of 150° C. or more, alternately 151° C. or more, alternately 152° C. or more, alternately 153° C. or more, alternately 154° C. or more, alternately 155° C. or more, alternately 156° C. or more, as determined by DSC.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:

1. In a first aspect of the invention there is provided a pyridyl-diamido transition metal complex (optionally for use in alkene polymerization) represented by the formula (A) or (B):

-continued

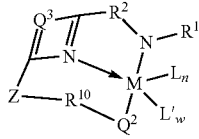

(B)

wherein:

M is a Group 3, 4, 5, 6, 7, 8, 9, 10, 11 or 12 metal;

$Q^1$ is a group that links $R^2$ and Z by a three atom bridge with the central of the three atoms being a group 15 or 16 element that preferably forms a dative bond to M preferably represented by the formula: -$G^1$-$G^2$-$G^3$- where $G^2$ is a group 15 or 16 atom, $G^1$ and $G^3$ are each a group 14, 15 or 16 atom, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$ and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is $NR^{17}$ or $PR^{17}$, where $R^{17}$ is selected from hydrocarbyl groups containing 1 to 20 carbon atoms (preferably from 2 to 16, preferably from 4 to 14, preferably from 5 to 12, preferably from 6 to 10) having a H/C ratio of 1.66 or more (alternately 1.70 or more, alternately 1.80 or more, alternately 1.83 or more) where the carbon atom bonded to the N or P is not a tertiary carbon atom, and where $R^{17}$ may be unsubstituted or substituted (preferably substituted with between one to five substituents that include F, Cl, Br, I, $CF_3$, $NO_2$, alkoxy, dialkylamino, silyl, siloxy, aryloxy, aryl, and alkyl groups having 1 to 10 carbons, such as methyl, ethyl, propyl, butyl, pentyl, hexyl, heptyl, octyl, nonyl, decyl, and isomers thereof);

$Q^3$ is -(TT)- or -(TTT)- where each T is carbon or a heteroatom (preferably C, O, S, or N, and said carbon or heteroatom may be unsubstituted (e.g. hydrogen is bound to the carbon or heteroatom) or substituted with one or more $R^{30}$ groups), that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —($R_{14}$)$_p$C—C($R_{15}$)$_q$— and $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n+w is no greater than 4.

2. The complex of paragraph 1, wherein $Q^1$ is a substituted or unsubstituted pyridine group linked to Z and $R^2$ through the carbons in the 2 and 6 position (of the pyridine ring, with the nitrogen being the 1 position).

3. The complex of paragraph 1 or 2, wherein $G^1$ and $G^3$ are each independently selected from C, N, O, and S, preferably $G^1$ and $G^3$ with their respective R groups are methyl, ethyl, propyl, butyl, pentyl, hexyl, octyl, and the like, preferably $G^1$ and $G^3$ with their respective R groups are formed into a ring structure, preferably pyridine.

4. The complex of paragraph 1, 2, or 3, wherein $Q^2$ is $NR^{17}$.

5. The complex of paragraph 1, 2, 3, or 4, wherein $Q^3$ is a three carbon linker (CH—CH—CH) that forms a pyridine ring or $Q^3$ is two atom linker containing one carbon and one group 15 or 16 element such that the linker forms a five-membered heterocycle, such as an imidazole or substituted imidazole.

6. A pyridyldiamido transition metal complex (optionally for use in alkene polymerization) represented by the formula (I) or (II):

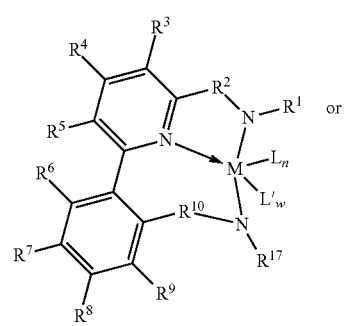

(I)

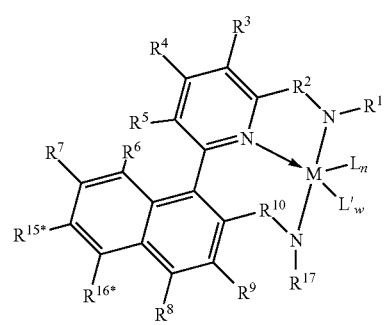

(II)

wherein:

M is a Group 3, 4, 5, 6, 7, 8, 9, 10, 11 or 12 metal;

$R^{17}$ is selected from hydrocarbyl groups containing 1 to 20 carbon atoms (preferably from 2 to 16, preferably from 4 to 14, preferably from 5 to 12, preferably from 6 to 10) having a H/C ratio of 1.66 or more (alternately 1.70 or more, alternately 1.80 or more, alternately 1.83 or more) where the carbon atom bonded to the N is not a tertiary carbon atom, and where $R^{17}$ may be unsubstituted or substituted (preferably substituted with between one to five substituents that include F, Cl, Br, I, $CF_3$, $NO_2$, alkoxy, dialkylamino, silyl, siloxy, aryloxy, aryl, and alkyl groups having 1 to 10 carbons, such as methyl, ethyl, propyl, butyl, pentyl, hexyl, heptyl, octyl, nonyl, decyl, and isomers thereof);

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n+w is no greater than 4;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings; and $R^6$, $R^7$, $R^8$, $R^9$, $R^{15*}$, and $R^{16*}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15*}$, and/or $R^{16*}$ & $R^{15*}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings.

7. The complex according to any of paragraphs 1 to 6 in which M is Ti, Zr, or Hf.

8. The complex according to any of paragraphs 1 to 7 in which $R^2$ is $CH_2$.

9. The complex according to any of paragraphs 1 to 8 in which $R^1$ and $R^3$ to $R^9$ and/or $R^{11}$ to $R^{15}$ above contain 1 to 30 carbon atoms, especially from 2 to 20 carbon atoms.

10. The complex according to any of paragraphs 1 to 9 in which E is carbon and $R^1$ and $R^{11}$ are independently selected from phenyl groups that are variously substituted with between zero to five substituents that include F, Cl, Br, I, $CF_3$, $NO_2$, alkoxy, dialkylamino, hydrocarbyl (such as alkyl and aryl), and substituted hydrocarbyls (such as heteroaryl), groups with from one to ten carbons.

11. The complex according to any of paragraphs 1 to 10 in which L is or are selected from halide, alkyl, aryl, alkoxy, amido, hydrido, phenoxy, hydroxy, silyl, allyl, alkenyl, and alkynyl; and/or L' is or are selected from ethers, thio-ethers, amines, nitriles, imines, pyridines, and phosphines.

12. The complex of any of paragraphs 1 to 11, wherein $R^2$ is represented by the formula:

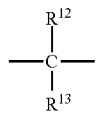

where $R^{12}$ is hydrogen, alkyl, aryl, or halogen; and $R^{13}$ is hydrogen, alkyl, aryl, or halogen.

13. The complex of any of paragraphs 1 to 12, wherein $R^6$, $R^7$, $R^8$, $R^9$, $R^{15*}$, and $R^{16*}$, are independently selected from the group consisting of hydrogen, hydrocarbyls, substituted hydrocarbyls, alkoxy, halogen, amino, and silyl.

14. The complex of any of paragraphs 1 to 13, wherein $R^1$, $R^3$, $R^4$, and $R^5$ each contain from 1 to 30 carbon atoms.

15. The complex of any of paragraphs 1 to 14, wherein E is carbon and $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

16. The complex of any of paragraphs 1 to 15, wherein for $R^{10}$, E is carbon, $R^{12}$ is phenyl and $R^{13}$ is H.

17. The complex of any of paragraphs 1 to 16, wherein the $R^2$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), and or the $R^{10}$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), where alkyl is a $C_1$ to $C_{40}$ alkyl group, aryl is a $C_5$ to $C_{40}$ aryl group, and Ph is phenyl.

18. The complex of any of paragraphs 1 to 17, wherein $R^{17}$ is cyclohexyl, cyclooctyl, cyclodecyl, or cyclododecyl.

19. The complex of any of paragraphs 1 to 18, wherein $R^{17}$ is substituted with between one, two, three, four, or five substituents selected from the group consisting of F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

20. A catalyst system comprising an activator and the complex of any of paragraphs 1 to 19.

21. The catalyst system of paragraph 20, wherein the activator is an alumoxane and/or a non-coordinating anion.

22. The catalyst system of paragraph 20 or 21, wherein the catalyst system is supported.

23. A polymerization process to produce a polyolefin comprising: a) contacting one or more olefin monomers with the catalyst system of paragraph 20, 21, or 22; and b) obtaining an olefin polymer, where the catalyst has an activity of 200 kg polymer/mmol of transition metal complex/hour or more.

24. The process of paragraph 23, wherein the monomer comprises ethylene and/or propylene.

25. The process of paragraph 23, wherein the monomer comprises propylene and the propylene polymer formed has a melting temperature of 150° C. or more as determined by differential scanning calorimetry.

26. A polymerization process to produce polyolefin comprising: a) contacting one or more olefin monomers with the catalyst system of claim 18; and b) obtaining olefin polymer, where the catalyst has an activity of 200 kg polymer/mmol transition metal/hour or more.

27. The process of paragraph 23, wherein the monomer comprises propylene and the propylene polymer formed has a Tm of 150° C. or more.
28. The complex of any of paragraph 11 to 17, wherein $R^{17}$ is methyl, ethyl, propyl, n-butyl, cyclohexyl, cyclooctyl, cyclodecyl, or cyclododecyl.
29. The complex of any of paragraph 11 to 17, wherein the carbon atom in the $R^{17}$ group in $Q_2$ of formula A or B bonded to the N or P is a secondary carbon atom or where the carbon atom in the $R^{17}$ group in formula I or II bonded to the N is a secondary carbon atom.
30. The complex of any of paragraph 11 to 17, wherein $R^{17}$ is a cyclic aliphatic hydrocarbon group.
31. A catalyst system comprising an activator and a pyridyldiamido transition metal complex of paragraph 6.
32. The catalyst system of paragraph 31, wherein the $R^{17}$ group(s) are selected from the group consisting of cyclopropyl, cyclopentyl, cyclohexyl, cyclooctyl, cyclodecyl, and cyclododecyl.
33. A polymerization process to produce polyolefin comprising: a) contacting one or more olefin monomers with the catalyst system of paragraph 31; and b) obtaining olefin polymer, where the catalyst has an activity of 200 kg polymer/mmol transition metal/hour or more.

EXAMPLES

The complexes A and B (inventive) were prepared as described below. Complex J was made analogously to complex A, but with the cyclohexylamine being substituted by cyclooctylamine. Complexes C and D (comparative) were prepared as described in US 2012/0071616. Complex K was prepared analogously to complex A, but using the pyridyldiamine ligand that was prepared as described in US 2012/0071616 A1.

A

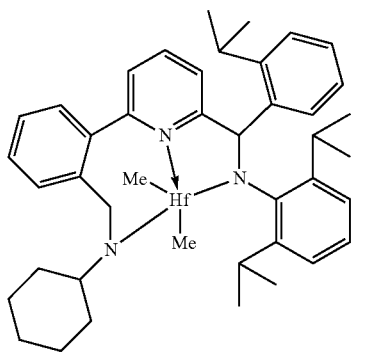

B

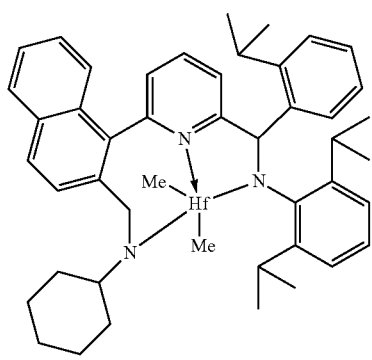

J

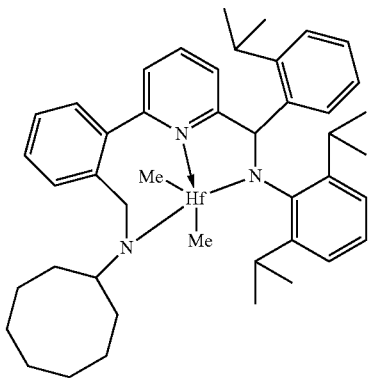

C

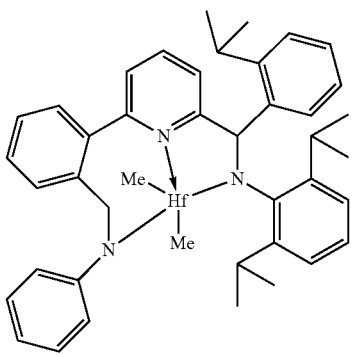

D

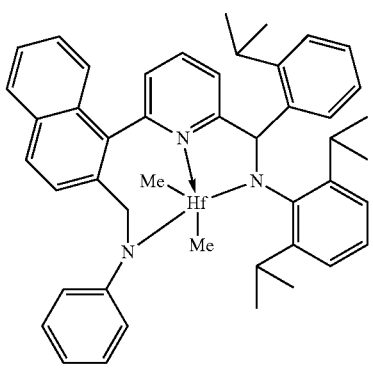

K

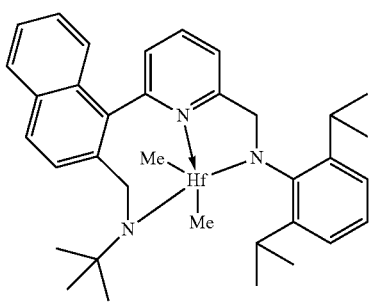

4,4,5,5-Tetramethyl-2-(2-methyl-1-naphthyl)-1,3,2-dioxaborolane (1). 1,2-Dibromoethane (~0.3 ml) was added to 6.10 g (0.25 mol) of magnesium turnings in 1000 cm³ of THF. This mixture was stirred for 10 min, and then 55.3 g (0.25 mol) of 1-bromo-2-methylnaphtalene was added by vigorous stirring for 3.5 h at room temperature. Further on, 46.5 g (250 mmol) of 2-isopropoxy-4,4,5,5-tetramethyl-1,3,2-dioxaborolane was added in one portion. The resulting mixture was stirred for 15 min and then poured into 1000 cm³ of cold water. The product was extracted with 3×300 ml of ethyl acetate. The organic layer was separated, washed by water, brine, dried over MgSO$_4$, and, finally, evaporated to dryness. The formed white solid was washed by 2×75 ml of pentane and then dried in vacuum. Yield 47.3 g (70%). Anal. calc. for C$_{17}$H$_{21}$BO$_2$: C, 76.14; H, 7.89. Found: C, 76.21; H, 7.96. $^1$H NMR (CDCl$_3$): δ 8.12 (m, 1H, 8-H), 7.77 (m, 1H, 5-H), 7.75 (d, J=8.4 Hz, 1H, 4-H), 7.44 (m, $^1$H, 7-H), 7.38 (m, 1H, 6-H), 7.28 (d, J=8.4 Hz, 1H, 3-H), 2.63 (s, 3H, 2-Me), 1.48 (s, $^{12}$H, CMe$_2$CMe$_2$).

2-[2-(Bromomethyl)-1-naphthyl]-4,4,5,5-tetramethyl-1,3,2-dioxaborolane (2). A mixture of 47.3 g (176 mmol) of 4,4,5,5-tetramethyl-2-(2-methyl-1-naphthyl)-1,3,2-dioxaborolane, 33.0 g (185 mmol) of NBS, and 0.17 g (0.70 mmol) of benzoyl peroxide in 340 ml of CCl$_4$ was stirred in argon atmosphere for 14 h at 75° C. The resulting mixture was cooled to room temperature, filtered through a glass frit (G3), and the filtrate was evaporated to dryness. This procedure gave 62.2 g (99%) of a beige solid. Anal. calc. for C$_{17}$H$_{20}$BBrO$_2$: C, 58.83; H, 5.81. Found: C, 58.75; H, 5.90. $^1$H NMR (CDCl$_3$): δ 8.30 (m, 1H, 8-H), 7.84 (d, J=8.3 Hz, 1H, 4-H), 7.79 (m, 1H, 5-H), 7.43-7.52 (m, 3H, 3,6,7-H), 4.96 (s, 2H, CH$_2$Br), 1.51 (s, 12H, CMe$_2$CMe$_2$).

Cyclohexyl{[4,4,5,5-tetramethyl-1,3,2-dioxaborolan-2-yl)-2-naphthyl]methyl}amine (3). A mixture of 18.0 g (181 mmol) of cyclohexylamine, 42.1 (129 mmol) g of 2-[2-(bromomethyl)-1-naphthyl]-4,4,5,5-tetramethyl-1,3,2-dioxaborolane, 18.4 g (133 mmol) of K$_2$CO$_3$, and 500 ml of DMF was stirred for 12 h at 80° C. in argon atmosphere. The resulting mixture was poured into 1200 ml of water. The product was extracted with 3×200 ml of ethyl acetate. The combined extract was dried over Na$_2$SO$_4$ and then evaporated to dryness. An excess of cyclohexylamine was distilled off using the Kugelrohr apparatus. Yield 29.9 g (67%) of a dark red glassy solid. Anal. Calc for C$_{23}$H$_{32}$BNO$_2$: C 75.62; H 8.83; N 3.83. Found: C 75.69; H 8.79; N 3.87. $^1$H NMR (CDCl$_3$): δ 8.51 (m, 1H, 8-H in naphtyl), 7.76 (m 1H, 4-H in naphtyl), 7.69 (m, 1H, 5-H in naphtyl), 7.41-7.46 (m, 1H, 7-H in naphtyl), 7.35-7.39 (m, 1H, 6-H in naphtyl), 7.18 (m, 1H, 3-H in naphtyl), 4.16 (s, 2H, CH$_2$), 3.32 (m, 1H, NH), 1.56-1.67 (m, 5H, Cy), 1.37 (s, 12H, BPin), 1.15-1.25 (m, 5H, Cy), 0.94-1.06 (m, 1H, Cy).

6-{2-[(Cyclohexylamino)methyl]-1-naphthyl}pyridine-2-carbaldehyde (4). A solution of 21.2 g (74.1 mmol) of Na$_2$CO$_3$×10H$_2$O in 660 ml of water and 190 ml of methanol was purged with argon for 30 min. The obtained solution was added to a mixture of 29.9 g (80.0 mmol) of cyclohexyl{[1-(4,4,5,5-tetramethyl-1,3,2-dioxaborolan-2-yl)-2-naphthyl]methyl}amine, 14.0 g (80.0 mmol) of 6-bromopyridine-2-carbaldehyde, 4.62 g (4.00 mmol) of Pd(PPh$_3$)$_4$, and 780 ml of toluene in argon atmosphere. This mixture was refluxed for 10 h using a mechanical stirrer, then cooled to room temperature. The organic layer was separated, dried over Na$_2$SO$_4$, evaporated to 300 ml in volume, and then extracted with 3×300 ml of 2M HCl. The combined aqueous layer was alkalified to pH 10 by the saturated aqueous K$_2$CO$_3$, and then extracted with 3×200 ml of dichloromethane. The combined organic extract was dried over Na$_2$SO$_4$ and evaporated to dryness. Yield 23.1 g (84%) of a brown oil. Anal. Calc for C$_{23}$H$_{24}$N$_2$O: C 80.20; H 7.02; N 8.13. Found: C 80.78; H 7.11; N 8.01. $^1$H NMR (CDCl$_3$): δ 10.08 (s, 1H, CHO), 7.96-8.03 (m, 2H, 3-H, 4-H in Py), 7.83-7.89 (m, 2H, 8,5-H in Py), 7.59-7.64 (m, 2H, 5-H in Py and 4-H in naphthyl), 7.39-7.43 (m, 1H, 6-H in naphthyl), 7.30-7.34 (m, 1H, 7-H in naphthyl), 7.20-7.23 (m, 1H, 3-H in naphthyl), 3.56 (m, 2H, CH$_2$), 2.21 (m, 1H, 1-H in Cy), 1.57-1.66 (m, 4H, Cy), 1.02-1.11 (m, 4H, Cy), 0.88-0.96 (m, 2H, Cy).

N-[(1E)-(6-{2-[(Cyclohexylamino)methyl]-1-naphthyl}pyridin-2-yl)methylene]-2,6-diisopropylaniline (5). A solution of 9.80 g (28.0 mmol) of 6-{2-[(cyclohexylamino)methyl]-1-naphthyl}pyridine-2-carbaldehyde, 5.55 g (31.0 mmol) of 2,6-diisopropylaniline, 0.1 g of TsOH in 100 ml of dry ethanol was refluxed for 10 h in argon atmosphere. The resulting mixture was cooled to room temperature and then evaporated to dryness. The residue was purified by flash chromatography on silica gel 60 (40-63 um, eluent: hexane-ethyl acetate-triethylamine=10:1:1, vol.). Yield 10.8 g (77%) of yellow powder. Anal. Calc for C$_{35}$H$_{41}$N$_3$: C 83.45; H 8.20; N 8.34. Found: C 83.59; H 8.06; N 8.41. $^1$H NMR (CDCl$_3$): δ 8.39 (m, 1H, 3-H in Py), 8.35 (s, 1H, CHN), 8.00 (m, 1H, 4-H in Py), 7.87-7.92 (m, 2H, 4,8-H in naphthyl), 7.63 (m, 1H, 3-H in naphthyl), 7.54 (m, 1H, 3-H in Py), 7.37-7.47 (m, 3H, 5-H in Py and 6,7-H in naphthyl), 7.09-7.17 (m, 3H, 3,4,5-H in naphthyl), 3.69 (m, 2H, CH$_2$N), 3.01 (sept, J=6.8 Hz, 2H, CH in 2,6-diisopropylphenyl), 2.29 (m, 1H, CH in Cy), 1.61-1.72 (m, 4H, Cy), 1.52-1.54 (m, 2H, Cy), 1.19 (d, J=6.8 Hz, 12H, CH$_3$ in 2,6-diisopropylphenyl), 1.09-1.11 (m, 2H, Cy), 0.94-0.99 (m, 2H, Cy).

N-[(6-{2-[(Cyclohexylamino)methyl]-1-naphthyl}pyridin-2-yl)(2-isopropylphenyl)methyl]-2,6-diisopropylaniline (6). To a solution of 3.56 g (18.0 mmol) of 2-isopropylbromobenzene in 80 ml of THF 21.0 ml (35.7 mmol) of 1.7M $^t$BuLi in pentane was added at −80° C. in argon atmosphere. The resulting solution was stirred for 1 h at this temperature. Then, a solution of 3.00 g (6.00 mmol) of N-[(1E)-(6-{2-[(cyclohexylamino)methyl]-1-naphthyl}pyridin-2-yl)methylene]-2,6-diisopropylaniline in 20 ml of THF was added. The obtained mixture was stirred for 30 min at −80° C. Further on, 10 ml of water was added, and this mixture was warmed to room temperature. The resulting mixture was diluted with 100 ml of water, and crude product was extracted with 50 ml of ethyl acetate. The organic layer was separated, dried over Na$_2$SO$_4$, and evaporated to dryness. The residue was purified by flash chromatography on silica gel 60 (40-63 um, eluent: hexane-ethyl acetate-triethylamine=10:1:1, vol.). Yield 1.15 g (31%) of a yellow glassy solid. Anal. Calc for C$_{44}$H$_{53}$N$_3$: C 84.70; H 8.56; N 6.73. Found: C 84.86; H 8.69; N 6.55. $^1$H NMR (CDCl$_3$): δ 7.87 (m); 7.59-7.74 (m); 7.42-7.46 (m); 7.14-7.34 (m); 6.99 (m); 5.52 (d); 5.39 (d); 4.80 (m); 4.50 (m); 3.67 (m); 3.48-3.58 (m); 3.18 (m); 2.98 (m); 2.50-2.55 (m); 2.15(m); 2.25 (m); 1.48-1.72 (m); 1.03-1.15 (m); 0.98-1.01 (m); 0.91-0.93 (m); 0.79-0.86 (m).

Complex B. While shielded from direct light, ligand 6 (0.898 g, 1.44 mmol), Hf(NMe$_2$)$_2$Cl$_2$(dme) (0.616 g, 1.44 mmol), and toluene (20 mL) were combined and heated to 95° C. in a round bottomed flask that was uncapped to allow for the release of dimethylamine After 3 h, the volatiles were evaporated under a stream of nitrogen to afford a yellow solid that was washed thoroughly with Et$_2$O to afford 1.11 g (1.27 mmol) of the dichloride complex. This dichloride intermediate was dissolved in CH$_2$Cl$_2$ (20 mL) and Me$_2$Mg in Et$_2$O (4.43 mL, 1.4 mmol) was added dropwise. After 30 minutes the volatiles were evaporated under a stream of nitrogen and the residue was dried thoroughly under reduced pressure. The residue was extracted with CH$_2$Cl$_2$ (10 mL) and filtered. Concentration of this solution to 1 mL followed by the addition of pentane (3 mL) caused the product to precipitate as a yellow microcrystalline solid. Yield 0.99 g, 83%. Room temperature H-NMR spectroscopic analysis indicates that the product is an 85:15 mixture of rotational diastereomers.

N-(2-(4,4,5,5-tetramethyl-1,3,2-dioxaborolan-2-yl)benzyl)cyclohexanamine (7). Toluene (250 mL) was added to 2-(4,4,5,5-tetramethyl-1,3,2-dioxaborolan-2-yl)benzaldehyde (5.0 g, 21.54 mmol) followed by cyclohexylamine (2.37 g, 23.89 mmol) and formic acid (~1.0 mL of 88%) to form a clear solution. The mixture was allowed to reflux using a Dean-Stark trap and the toluene/water mixture collected till clear. Upon completion, the mixture was cooled to room temperature and the solution evaporated to 100 mL. MeOH (200 mL) was then added to the reaction mixture followed by $NaBH_4$ (1.63 g, 43.08 mmol) portion wise. The mixture was stirred for 20 min and quenched with water (5 mL). The solution was evaporated to 100 mL and EtOAc (50 mL) was added. The solution was dried with $Na_2SO_4$ and the solvent removed by reduced pressure, yielding a white solid. $Et_2O$ (200 mL) was then added dissolving half of the white solid. The remaining solid was collected and dried under reduced pressure offering compound 7. Yield: 6.3 g, 46.4%. $^1H$ NMR $(CD_2Cl_2)$: δ 7.52-7.50 (d, 1H), 7.28-7.27 (m, 2H), 7.15-7.13 (d, 1H), 4.02 (s, 2H), 3.42 (s, 1H), 3.15-3.07 (m, 1H), 1.74-1.61 (m, 5H), 1.29 (s, 12H), 1.19-1.05 (m, 6H).

6-(2-((cyclohexylamino)methyl)phenyl)picolinaldehyde (8). MeOH (90 mL) and water (300 mL) were added to $Na_2CO_3$ (2.97 g, 28.0 mmol) and purged with $N_2$ for 30 min. The obtained solution was added to a mixture of compound 7 (7.95 g, 25.2 mmol), 6-bromopyridine-2-carbaldehyde (4.70 g, 25.2 mmol) and $Pd(PPh_3)_4$ (1.48 g, 1.28 mmol) dissolved in toluene (300 mL) under $N_2$ atmosphere. The mixture was allowed to reflux for 12 h and then cooled to room temperature. The organic layer was separated, dried with $Na_2SO_4$, evaporated to 100 mL and extracted with 2M HCl (3×100 mL). Saturated aqueous $K_2CO_3$ was added to the combined aqueous layer until a pH 8 was reached and extracted with dichloromethane (3×100 mL). The combined organic extract was dried with $Na_2SO_4$ and evaporated under reduced pressure. The product was isolated by column chromatography on silica gel using dichloromethane-EtOAc (80:20, v/v) as eluent offering compound 8. Yield: 1.30 g, 17.5%. $^1H$ NMR $(CD_2Cl_2)$: δ 10.15 (s, 1H), 7.98-7.96 (m, 2H), 7.93-7.91 (d, 1H), 7.57-7.52 (m, 2H), 7.49-7.39 (m, 2H), 3.81 (s, 2H), 2-.49-2.43 (m, 1H), 1.87-1.84 (m, 5H), 1.30-1.02 (m, 6H).

N-((6-(2-((cyclohexylamino)methyl)phenyl)pyridin-2-yl) methylene)-2,6-diisopropylaniline (9). Toluene (250 mL) as added to compound 8 (1.44 g, 4.89 mmol) and 2,6-diisopropylaniline (0.870 g, 4.90 mmol), followed by formic acid (5 mL). The mixture was allowed to reflux using a Dean-Stark trap and the toluene/water mixture collected till clear. The resulting mixture was cooled to room temperature, washed with water (100 mL), dried with brine and $Na_2SO_4$ and evaporated under reduced pressure. The product was isolated by column chromatography on silica gel using Hexane-EtOAc (85:15, v/v) as eluent offering compound 9. Yield: 0.460 g, 20.7%. $^1H$ NMR $(CD_2Cl_2)$: δ 7.97-7.94 (s, 1H), 7.74 (d, 1H), 7.72 (t, 1H), 7.53 (d, 1H), 7.50-7.49 (t, 2H), 7.45-7.37 (m, 2H), 7.22-7.16 (d, 2H), 7.15-7.13 (t, 1H), 3.83 (s, 2H), 3.09-2.99 (sept, 2H), 2.43-2.36 (m, 1H), 1.79-1.55 (m, 6H), 1.23-1.21 (d, 12H), 1.18-0.98 (m, 5H).

N-((6-(2-((cyclohexylamino)methyl)phenyl)pyridin-2-yl) (2-isopropylphenyl)methyl)-2,6-diisopropylaniline (10). $Et_2O$ (10 mL) was added to compound 9 (0.189 g, 0.417 mmol) to form a clear pale yellow solution. At −80° C., an $Et_2O$ (5 mL) solution of 2-isopropylphenyllithium (0.136 g, 1.08 mmol) was added dropwise to form a red-purple solution. The mixture was allowed to slowly warm to ambient temperature overnight. Water (50 mL) was then added followed by $Et_2O$ (50 mL). The organics were separated, dried with brine and then $MgSO_4$. Evaporation of the volatiles afforded compound 10, which did not require any purification. Yield: 0.224 g, 76.2%. $^1H$ NMR $(CD_2Cl_2)$: δ 7.67 (t, 2H), 7.1-7.53 (m, 10H), 7.00 (m, 3H), 5.44 (d, 1H), 4.40 (d, 1H), 3.69 (s, 2H), 3.11 (sept, 1H), 2.91 (sept, 2H), 2.24 (m, 1H), 1.5-1.7 (m, 6H), 1.25 (d, 3H), 1.1-1.2 (m, 4H), 0.97 (d, 12H), 0.93 (d, 6H).

Complex A. While shielded from direct light, ligand 10 (0.224 g, 0.390 mmol), $Hf(NMe_2)_2Cl_2(dme)$ (0.167 g, 0.390 mmol), and toluene (10 mL) were combined and heated to 95° C. in a glass vial that was loosely capped with aluminum foil to allow for the release of dimethylamine After 4 h, the volatiles were evaporated under a stream of nitrogen to afford a yellow solid that was washed thoroughly with pentane to afford 0.236 g (0.287 mmol) of the dichloride complex. This dichloride intermediate was dissolved in $CH_2Cl_2$ (6 mL) and $Me_2Mg$ in $Et_2O$ (1.09 mL, 0.344 mmol) was added dropwise. After 30 minutes the volatiles were evaporated under a stream of nitrogen and the residue was dried thoroughly under reduced pressure. The residue was extracted with $CH_2Cl_2$ (5 mL) and filtered. Concentration of this solution to an oily residue followed by the addition of pentane (3 mL) caused the product to form yellow-orange crystals. Yield 0.192 g, 63.1%.

Polymerizations Examples

Shown in Table 1 are propylene polymerization data complexes A, B, and J and comparative complexes C, D, and K. From these data it is shown that the catalysts formed by the activation of complexes A, B, and J have unexpectedly significantly higher activity than the comparative examples. Additionally polypropylene formed by complexes A, B, and J have unexpectedly higher melting points than the polypropylene prepared by comparative complexes C, D, and K. For example, comparing run 1 with run 3 (Table 1), it is observed that the catalyst formed from complex A has over 4 times the activity of the catalyst formed by complex C (comparative). Thus, it can be concluded that the substitution of a phenyl group of complex C for a cyclohexyl group (to give complex A) is unexpectedly advantageous. Additionally the polypropylene produced in run 1 has a 15° C. higher melting point than that produced in run 3. Comparing run 5 to run 6 (Table 1) we see a similar trend. It is observed that the catalyst formed by complex B is nearly 3 times as active as the catalyst formed by complex D (comparative). Additionally, the melting point of the polypropylene formed in run 5 is over 7° C. higher than that formed in run 6 (comparative). Thus, it can be concluded that the substitution of a phenyl group of complex D for a cyclohexyl group (to give complex B) is unexpectedly advantageous. The same trends hold for polymerizations performed at 100° C. (Table 1). Comparing run 7 to run 9 it is observed that the catalyst formed from complex A is more active than the catalyst formed from complex C (comparative). The polypropylene formed in run 7 also has a higher melting point than the polypropylene formed in run 9 (comparative). Thus, it can be concluded that the substitution of a phenyl group of complex C for a cyclohexyl group (to give complex A) is unexpectedly advantageous. Comparing run 8 to run 10 it is observed that the catalyst formed from complex B is more active than the catalyst formed from complex D (comparative). The polypropylene formed in run 8 also has a higher melting point than the polypropylene formed in run 10 (comparative). Thus, it can be concluded that the substitution of a phenyl group of complex D for a cyclohexyl group (to give complex B) is unexpectedly advantageous.

The catalyst formed by the activation of comparative complex K was found to have much lower activity for propylene polymerization than the other complexes. As shown in runs 14-16, the catalyst yielded only trace amounts of polypropylene. Thus, substitution at $R^{17}$ with tertiary butyl was not advantageous.

General Polymerization Procedures

Unless stated otherwise propylene polymerizations were carried out in a parallel, pressure reactor, as generally described in U.S. Pat. Nos. 6,306,658; 6,455,316; 6,489,168; WO 00/09255; and Murphy et al., J. Am. Chem. Soc., 2003, 125, pages 4306-4317, each of which is fully incorporated herein by reference for US purposes. Although the specific quantities, temperatures, solvents, reactants, reactant ratios, pressures, and other variables are frequently changed from one polymerization run to the next, the following describes a typical polymerization performed in a parallel, pressure reactor. Table 1 below reports specific runs.

A pre-weighed glass vial insert and disposable stirring paddle were fitted to each reaction vessel of the reactor, which contains 48 individual reaction vessels. Then solvent (typically isohexane) was added to bring the total reaction volume, including the subsequent additions, to 4 mL. Propylene gas was introduced and the reactor vessels were heated to their set temperature. At this time scavenger and/or co-catalyst and/or a chain transfer agent, such as tri-n-octylaluminum in toluene (typically 100-1000 nmol) was added.

The contents of the vessel were stirred at 800 rpm. An activator solution (1.1 molar equivalents of N,N dimethyl anilinium tetrakis-pentafluorophenyl borate dissolved in toluene) was then injected into the reaction vessel along with 500 microliters of toluene, followed by a toluene solution of catalyst (typically 0.40 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a predetermined amount of pressure had been taken up by the reaction or a set amount of time had elapsed. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an infrared absorption or evaporative light scattering (run 19 only) detector. The molecular weights presented are relative to linear polystyrene standards and are uncorrected.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

TABLE 1

Propylene homopolymerizations. General conditions: N,N-dimethylanilinum tetrakis(perfluorophenyl)borate (1.1 equiv/Hf), tri-n-octylaluminum (300 nmol) isohexane solvent.

| run | catalyst | T (° C.) | pressure (psi) | time (s) | yield (mg) | Hf (mmol) | activity (kg/mmol/h) | Mw (g/mol) | Mn (g/mol) | Tm (1st melt, ° C.) |
|---|---|---|---|---|---|---|---|---|---|---|
| 1 | A | 70 | 120 | 46 | 206 | 0.00004 | 407 | 890,000 | 357,000 | 158.5 |
| 2 | B | 70 | 120 | 52 | 207 | 0.00004 | 356 | 701,000 | 286,000 | 158.2 |
| 3* | C | 70 | 120 | 104 | 209 | 0.00008 | 91 | 804,000 | 429,000 | 143.4 |
| 4 | A | 85 | 130 | 34 | 154 | 0.00004 | 402 | 493,000 | 217,000 | 154.2 |
| 5 | B | 85 | 130 | 45 | 154 | 0.00004 | 305 | 344,000 | 169,000 | 155.5 |
| 6* | D | 85 | 130 | 85 | 100 | 0.00004 | 106 | 248,000 | 172,000 | 148.8 |
| 7 | A | 100 | 140 | 68 | 85 | 0.00004 | 112 | 252,000 | 135,000 | 151.9 |
| 8 | B | 100 | 140 | 54 | 82 | 0.00004 | 137 | 146,000 | 74,000 | 154.5 |
| 9* | C | 100 | 140 | 69 | 103 | 0.00008 | 67 | 190,000 | 102,000 | 139.9 |
| 10* | D | 100 | 140 | 230 | 66 | 0.00004 | 26 | 93,000 | 66,000 | 145.5 |
| 11 | J | 70 | 120 | 41 | 195 | 0.00004 | 426 | 912,000 | 382,000 | 158.6 |
| 12 | J | 85 | 130 | 47 | 131 | 0.00004 | 252 | 572,000 | 273,000 | 156.2 |
| 13 | J | 100 | 140 | 75 | 68 | 0.00004 | 85 | 246,000 | 128,000 | 153.4 |
| 14* | K | 70 | 120 | 1200 | 11 | 0.00004 | 0.8 | 11,000 | 5,600 | 120.4 |
| 15* | K | 85 | 130 | 1200 | 5 | 0.00004 | 0.3 | n.d. | n.d. | n.d. |
| 16* | K | 100 | 140 | 1200 | 1 | 0.00004 | 0.1 | n.d. | n.d. | n.d. |

*Comparative examples.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element, or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A pyridyldiamido transition metal complex having the general formula (A) or (B):

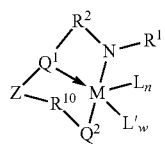

(A)

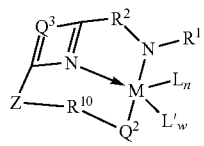

(B)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that may form a dative bond to M represented by the formula: $-G^1-G^2-G^3-$ where $G^2$ is a group 15 or 16 atom, $G^1$ and $G^3$ are each a group 14, 15 or 16 atom, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$ and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is $NR^{17}$ or $PR^{17}$, where $R^{17}$ is selected from cyclic non-aromatic hydrocarbyl groups containin-up to 20 carbon atoms, where the carbon atom bonded to the N or P is not a tertiary carbon atom, and where $R^{17}$ may be unsubstituted or substituted;

$Q^3$ is -(TT)- or -(TTT)- where each T is carbon or a heteroatom and said carbon or heteroatom may be unsubstituted or substituted with one or more $R^{30}$ groups, that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —($R_{14}$)$_p$C—C($R_{15}$)$_q$— and $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n+w is no greater than 4.

2. The pyridyldiamido transition metal complex of claim 1, wherein the complex is represented by the formula (I) or (II):

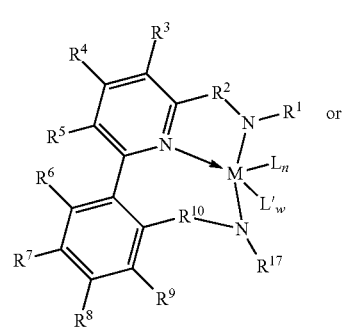

(I)

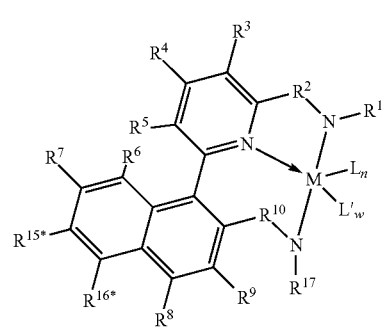

(II)

wherein:

M is a Group 3, 4, 5, 6, 7, 8, 9, 10, 11, or 12 metal;

where $R^{17}$ is selected from cyclic non-aromatic hydrocarbyl groups containing up to 20 carbon atoms, where the carbon atom bonded to the N is not a tertiary carbon atom, and where $R^{17}$ may be unsubstituted or substituted;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3, or 4;

wherein n+w is no greater than 4;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings; and $R^6$, $R^7$, $R^8$, $R^9$, $R^{15*}$, and $R^{16*}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15*}$, and/or $R^{16*}$ & $R^{15*}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings.

3. The complex of claim 1, wherein M is Ti, Zr, or Hf.

4. The complex of claim 1, wherein $R^2$ is represented by the formula:

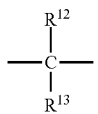

where $R^{12}$ is hydrogen, alkyl, aryl, or halogen; and $R^{13}$ is hydrogen, alkyl, aryl, or halogen.

5. The complex of claim 1, wherein each L is independently selected from the group consisting of halide, alkyl, aryl, alkoxy, amido, hydrido, phenoxy, hydroxy, silyl, allyl, alkenyl, and alkynyl.

6. The complex of claim 1, wherein each L' is independently selected from the group consisting of ethers, thioethers, amines, nitriles, imines, pyridines, and phosphines.

7. The complex of claim 1, wherein the $R^2$ group(s) are selected from the group consisting of $CH_2$, $CMe_2$, $SiMe_2$, $SiEt_2$, $SiPr_2$, $SiBu_2$, $SiPh_2$, $Si(aryl)_2$, $Si(alkyl)_2$, $CH(aryl)$, $CH(Ph)$, $CH(alkyl)$, and $CH(2\text{-isopropylphenyl})$, where alkyl is a $C_1$ to $C_{40}$ alkyl group, aryl is a $C_5$ to $C_{40}$ aryl group.

8. The complex of claim 1, wherein the $R^{10}$ group(s) are selected from the group consisting of $CH_2$, $CMe_2$, $SiMe_2$, $SiEt_2$, $SiPr_2$, $SiBu_2$, $SiPh_2$, $Si(aryl)_2$, $Si(alkyl)_2$, $CH(aryl)$, $CH(Ph)$, $CH(alkyl)$, and $CH(2\text{-isopropylphenyl})$, where alkyl is a $C_1$ to $C_{40}$ alkyl group, aryl is a $C_5$ to $C_{40}$ aryl group, and Ph is phenyl.

9. The complex of claim 1, wherein $R^{17}$ is cyclohexyl, cyclooctyl, cyclodecyl, or cyclododecyl.

10. The complex of claim 1, wherein M is Hf.

11. The complex of claim 1, wherein M is Hf and the $R^{17}$ group is selected from the group consisting of cyclopropyl, cyclopentyl, cyclohexyl, cyclooctyl, cyclodecyl, and cyclododecyl.

12. A catalyst system comprising an activator and a pyridyldiamido transition metal complex of claim 1.

13. The catalyst system of claim 12, wherein the activator is an alumoxane.

14. The catalyst system of claim 12, wherein the activator is a non-coordinating anion.

15. The catalyst system of claim 12, wherein the activator is a non-coordinating anion selected from the group consisting of: N,N-dimethylanilinium tetrakis(perfluorophenyl)borate, methyldioctadecylammonium tetrakis(perfluorophenyl)borate, methyldi($C_{14\text{-}20}$ alkyl)ammonium tetrakis(perfluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropylium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis (perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropylium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis (perfluorobiphenyl)borate, benzene(diazonium) tetrakis (perfluorobiphenyl)borate, and [4-t-butyl-PhNMe$_2$H][($C_6F_3(C_6F_5)_2)_4$B], (where Ph is phenyl, and Me is methyl).

16. A polymerization process to produce polyolefin comprising: a) contacting one or more olefin monomers with the catalyst system of claim 12; and b) obtaining olefin polymer, where the catalyst has an activity of 200 kg polymer/mmol transition metal/hour or more.

17. The process of claim 16, wherein the activator is an alumoxane.

18. The process of claim 16, wherein the activator is a non-coordinating anion.

19. The process of claim 16, wherein the monomer comprises ethylene.

20. The process of claim 16, wherein the monomer comprises propylene.

21. The process of claim 16, wherein the pyridyldiamido transition metal complex is supported.

22. The process of claim 16, wherein the monomer comprises propylene and the propylene polymer formed has a Tm of 150° C. or more.

23. A polymerization process to produce polyolefin comprising: a) contacting one or more olefin monomers with the catalyst system of claim 15; and b) obtaining olefin polymer, where the catalyst has an activity of 200 kg polymer/mmol transition metal/hour or more.

24. The complex of claim 2, wherein $R^6$, $R^7$, $R^8$, $R^9$, $R^{15*}$, and $R^{16*}$ are independently selected from the group consisting of hydrogen, hydrocarbyls, substituted hydrocarbyls, alkoxy, halogen, amino, and silyl.

25. The complex of claim 2, wherein $R^1$, $R^3$, $R^4$, and $R^5$ each contain from 1 to 30 carbon atoms.

26. The complex of claim 2, wherein E is carbon and $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

27. The complex of claim 2, wherein the carbon atom in the $R^{17}$ group in $Q_2$ of formula A or B bonded to the N or P is a secondary carbon atom or where the carbon atom in the $R^{17}$ group in formula I or II bonded to the N is a secondary carbon atom.

28. The complex of claim 2, wherein $R^{17}$ is cyclohexyl, cyclooctyl, cyclodecyl, or cyclododecyl.

29. The complex of claim 2, wherein the carbon atom in the $R^{17}$ group in $Q_2$ of formula A or B bonded to the N or P is a secondary carbon atom or where the carbon atom in the $R^{17}$ group in formula I or II bonded to the N is a secondary carbon atom.

30. The complex of claim 2, wherein $R^{17}$ is a substituted non aromatic $C_5$ to $C_{12}$ cyclic group.

31. The complex of claim 2, wherein M is Hf.

32. A catalyst system comprising an activator and a pyridyldiamido transition metal complex of claim 2.

33. The catalyst system of claim 32, wherein the $R^{17}$ group(s) are selected from the group consisting of cyclopropyl, cyclopentyl, cyclohexyl, cyclooctyl, cyclodecyl, and cyclododecyl.

34. The catalyst system of claim 33, where M is Hf.

35. The catalyst system of claim 32, where M is Hf.

36. A polymerization process to produce polyolefin comprising: a) contacting one or more olefin monomers with the catalyst system of claim 32; and b) obtaining olefin polymer, where the catalyst has an activity of 200 kg polymer/mmol transition metal/hour or more.

37. The polymerization process of claim 36, where M is Hf.

38. A pyridyldiamido transition metal complex having the general formula (A) or (B):

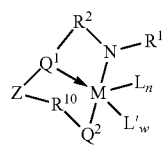

(A)

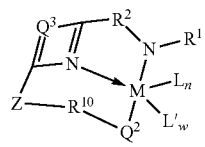

(B)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that may form a dative bond to M represented by the formula: $-G^1-G^2-G^3-$ where $G^2$ is a group 15 or 16 atom, $G^1$ and $G^3$ are each a group 14, 15 or 16 atom, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$ and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is $NR^{17}$ or $PR^{17}$, where $R^{17}$ is a cyclic aliphatic hydrocarbon group, having an H/C ratio that is 1.66 or more, where the carbon atom bonded to the N or P is not a tertiary carbon atom, and where $R^{17}$ may be unsubstituted or substituted;

$Q^3$ is -(TT)- or -(TTT)- where each T is carbon or a heteroatom and said carbon or heteroatom may be unsubstituted or substituted with one or more $R^{30}$ groups, that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^2$ and $R^{10}$ are each, independently, -E$(R^{12})(R^{13})$- with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —$(R_{14})_p$C—C$(R_{15})_q$— and $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n +w is no greater than 4.

39. The complex of claim 38, wherein $R^{17}$ is cyclopropyl, cyclobutyl, cyclopentyl, cyclohexyl, cycloheptyl, cyclooctyl, cyclononyl, cyclodecyl, cyclododecyl, or an isomer thereof.

40. A catalyst system comprising an activator and a pyridyldiamido transition metal complex of claim 38.

41. A polymerization process to produce polyolefin comprising: a) contacting one or more olefin monomers with the catalyst system of claim 40; and b) obtaining olefin polymer, where the catalyst has an activity of 200 kg polymer/mmol transition metal/hour or more.

42. A catalyst system comprising an activator and a pyridyldiamido transition metal complex having the general formula (A) or (B):

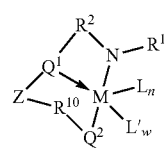

(A)

-continued

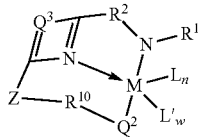

(B)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that may form a dative bond to M represented by the formula: $-G^1-G^2-G^3-$ where $G^2$ is a group 15 or 16 atom, $G^1$ and $G^3$ are each a group 14, 15 or 16 atom, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$ and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is $NR^{17}$ or $PR^{17}$, where $R^{17}$ is selected from the group consisting of cyclopropyl, cyclopentyl, cyclohexyl, cyclooctyl, cyclodecyl, and cyclododecyl, where the carbon atom bonded to the N or P is not a tertiary carbon atom, and where $R^{17}$ may be unsubstituted or substituted;

$Q^3$ is -(TT)- or -(TTT)- where each T is carbon or a heteroatom and said carbon or heteroatom may be unsubstituted or substituted with one or more $R^{30}$ groups, that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^2$ and $R^{10}$ are each, independently, $-E(R^{12})(R^{13})-$ with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is $-(R_{14})_p C-C(R_{15})_q-$ and $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings, p is 1 or 2, and q is 1 or 2;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4;

wherein n +w is no greater than 4.

* * * * *